United States Patent [19]

Arnaud et al.

[11] Patent Number: 5,188,748
[45] Date of Patent: Feb. 23, 1993

[54] AZEOTROPIC MIXTURES OF DIMETHYL ETHER AND OF 1,1,1,2-TETRAFLUOROETHANE AND THEIR USE

[75] Inventors: Didier Arnaud, Courbevoie; Jean-Claude Tanguy, Sannois, both of France

[73] Assignee: Societe Atochem, Puteaux, France

[21] Appl. No.: 658,271

[22] Filed: Feb. 20, 1991

[30] Foreign Application Priority Data

Feb. 20, 1990 [FR] France ................. 90 02012

[51] Int. Cl.$^5$ .......................... C09K 5/04; C09K 3/30
[52] U.S. Cl. ................................. 252/67; 252/162;
252/170; 252/171; 252/172; 252/305; 252/364;
252/DIG. 9; 62/114; 264/53; 264/DIG. 5;
521/88; 521/98; 521/131
[58] Field of Search .............. 252/162, 170, 171, 172,
252/305, 364, 67, 69, DIG. 9; 62/114;
264/DIG. 5, 53; 521/88, 98, 131

[56] References Cited

U.S. PATENT DOCUMENTS

| | | | |
|---|---|---|---|
| 2,885,427 | 5/1959 | Ruh et al. | 570/168 |
| 3,607,755 | 9/1971 | Murphy et al. | 252/67 |
| 4,129,603 | 12/1978 | Bell | 570/169 |
| 4,226,976 | 10/1980 | Goodman et al. | 528/498 |
| 4,428,854 | 1/1984 | Enjo et al. | 252/69 |
| 4,755,316 | 7/1988 | Magid et al. | 252/68 |
| 4,771,080 | 9/1988 | Ibuki et al. | 521/56 |
| 4,783,276 | 11/1988 | Bohnenn | 252/67 |
| 4,810,316 | 3/1989 | Wakabayashi et al. | 156/78 |

FOREIGN PATENT DOCUMENTS

| | | |
|---|---|---|
| 30127 | 6/1981 | European Pat. Off. . |
| 78-29937A | 4/1978 | World Int. Prop. O. . |
| 91/13968 | 9/1991 | World Int. Prop. O. . |

OTHER PUBLICATIONS

Chem. Abstr., vol. 87, 1977, Abstract No. 200710q.
"Technical Progress on Protecting the Ozone Layer, Refrigeration, Air Conditioning and Heat Pumpts", Technical Options Report, May 1989, pp. 34-36.

*Primary Examiner*—Christine Skane
*Attorney, Agent, or Firm*—Morgan & Finnegan

[57] ABSTRACT

This invention proposes to employ a mixture of dimethyl ether and of 1,1,1,2-tetrafluoroethane as refrigerant fluids to replace chlorofluorocarbons.

These compounds form an azeotrope which, at its normal boiling point (approximately −22.4° C. at 1.013 bar), contains approximately 62.3 mass % of 1,1,1,2-tetrafluoroethane.

The mixture according to the invention can also be employed as aerosol propellant or as blowing agent for plastic foams.

4 Claims, 2 Drawing Sheets

LIQUID/VAPOR EQUILIBRIUM CURVE
HFA 134a/DME MIXTURES
AT 20.2°C

AZEOTROPIC MIXTURES OF DIMETHYL ETHER AND OF 1,1,1,2-TETRAFLUOROETHANE AND THEIR USE

FIELD OF THE INVENTION

This present invention relates to mixtures of refrigerant fluids of low boiling point, which have no effect on stratosphericozone and which can be employed to replace chlorofluorocarbons (CFC) in compression refrigeration systems, especially household ones.

BACKGROUND OF THE INVENTION

It has now been established that, because of their high coefficient of action on ozone, CFCs will have to be replaced in the long term by refrigerant fluids which do not contain chlorine and which consequently have no effect on stratospheric ozone.

1,1,1,2-Tetrafluoroethane (HFA 134a) has already been proposed as a substitute for dichlorodifluoromethane (CFC 12). However, bearing in mind its thermodynamic performance which is lower than that of CFC 12 (in particular its coefficient of performance) HFA 134a does not represent a fully satisfactory solution if the running costs of a refrigerating plant are to be reduced to a minimum; this is particularly the case with household compression refrigerators which at present employ CFC 12 as refrigerant fluid and for which the designers are subjected to increasingly great energy consumption constraints.

DESCRIPTION OF THE INVENTION

The term "coefficient of performance" (COP) refers here and in what follows to the ratio of the cooling capacity of the refrigerant fluid to the theoretical compression work needed to compress the refrigerant fluid vapor. The coefficient of performance of the plant depends directly on this coefficient of performance relating to the fluid.

It has now been found that mixtures of dimethyl ether (DME) and of 1,1,1-2-tetrafluoroethane (HFA 134a) exhibit coefficients of performance which are higher than pure HFA 134a. In particular, it was found that in the case of mass fractions of HFA 134a of between 5% and 65% and of DME of between 35% and 95%, the mixture exhibits a pseudoazeotropic behavior resulting in a substantial and exceptionally stable gain in the coefficient of performance.

It was also found that DME and HFA 134a form an azeotrope with a maximum boiling point equal to approximately −22.4° C. at 1.013 bar and whose HFA 134a content at the normal boiling point is approximately 62.3% on a mass basis. This composition naturally varies as a function of the pressure of the mixture and, at a given pressure, can be easily determined using well-known techniques.

Because of the high value of their coefficients of performance, the refrigerant fluids employed will be advantageously mixtures containing, on a mass basis, from approximately 5% to 85% of HFA 134a (preferably approximately from 5 to 65%) and from approximately 15 to 95% of DME (preferably approximately from 35 to 95%). A very particularly preferred refrigerant mixture is the azeotrope described above.

Bearing in mind their physical properties which are close to those of the CFCs, the mixtures according to the invention can also be employed as aerosol propellants or as blowing agents in plastic foams.

EXAMPLES

The following examples illustrate the invention without limiting it.

EXAMPLE 1

The azeotrope according to the invention has been investigated experimentally at various temperatures by analysis, using gas phase chromatography, of the compositions of the liquid phase and of the vapor phase for various mixtures of HFA 134a and of DME.

The pressures were measured with an accuracy better than 0.02 bar by means of a Heise manometer. The temperatures were measured to within 0.02° C. by means of a 1000-ohm platinum probe.

Figure 1:
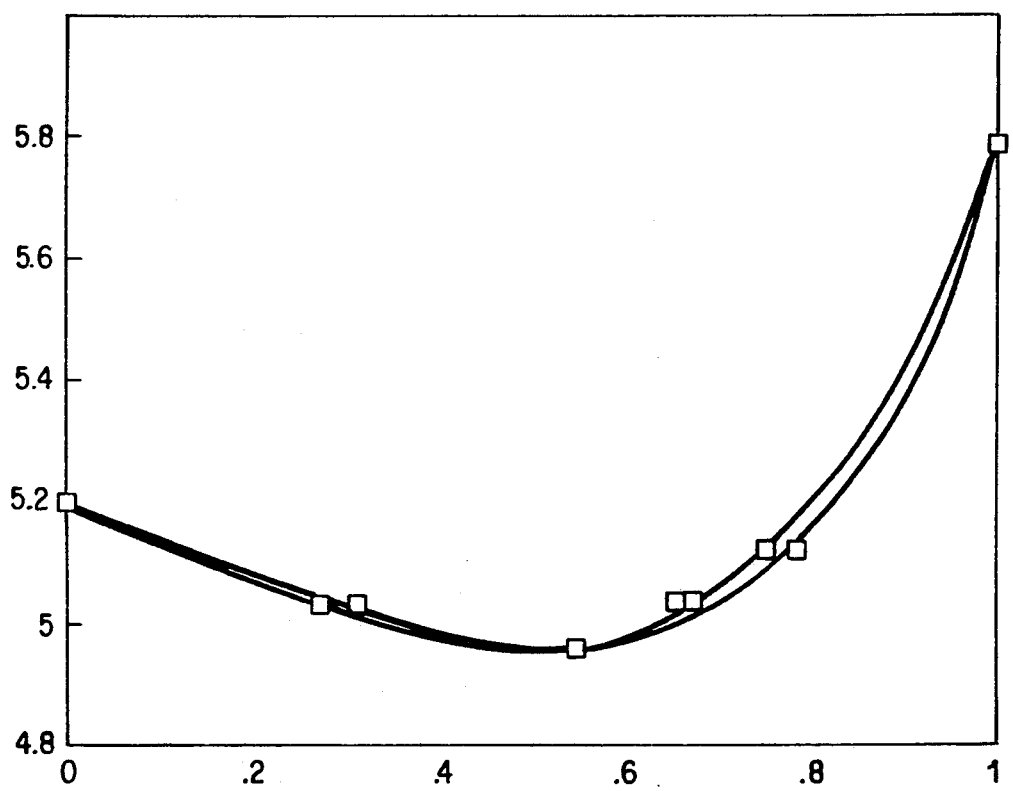
FIG. 1 is a graph showing the liquid/vapor equilibrium curve for HFA 134a/DME mixtures.

FIG. 1 contains a graph which shows the liquid/vapor equilibrium curve for HFA 134a/DME mixtures, established at the temperature of 20.2° C. In this graph the abscissa axis shows the mass fraction of HFA 134a and the ordinate axis the absolute pressure in bars; the symbols □ correspond to the experimental points.

A curve similar to that of shown on FIG. 1 is obtained for each temperature. On successive additions of HFA 134a to the DME, the pressure developed by the mixture decreases steadily and then passes through a minimum and increases steadily, which demonstrates the existence of the azeotrope with a maximum boiling point.

The correlation of the experimental points obtained in this way for several isotherms was obtained using well-known techniques, by means of a data-processing simulation.

The normal boiling points thus determined for various HFA 134a compositions are summarized in the following Table 1:

TABLE 1

| Composition, mass % of HFA 134a | Normal boiling point °C. |
| --- | --- |
| 100 | −25.80 |
| 90 | −24.12 |
| 80 | −23.04 |
| 70 | −22.51 |
| 60 | −22.41 |
| 62.3 | −22.40 |
| 50 | −22.60 |
| 40 | −22.97 |
| 30 | −23.43 |
| 20 | −23.92 |
| 10 | −24.40 |
| 0 | −24.85 |

The results of these correlations demonstrate the normal boiling point maximum in the case of a mass fraction of HFA 134a equal to 62.3%, and this enables the azeotrope to be characterized by:

- its normal boiling point, which is equal to approximately −22.4° C.
- its mass composition, equal to approximately 62.3% of HFA 134a.

Table 2, which follows, gives the pressure/temperature relationship for this azeotrope, compared with that of the pure substances.

TABLE 2

| Temperature (°C.) | Absolute pressure (bar) | | |
|---|---|---|---|
| | DME/HFA 134a azeotrope | pure HFA 134a | pure DME |
| −20.0 | 1.12 | 1.31 | 1.24 |
| 5.8 | 3.08 | 3.62 | 3.28 |
| 20.2 | 4.96 | 5.79 | 5.20 |
| 50.0 | 11.50 | 13.40 | 11.70 |

The vapor pressure of the azeotrope remains lower than the vapor pressure of the pure substances over a wide temperature range; these data show that the mixture remains azeotropic throughout this temperature range.

Furthermore, for mass compositions varying between 5 and 65% of HFA 134a, the vapor pressure of the mixture remains exceptionally stable (a change of less than 4%). This demonstrates the pseudoazeotropic behavior of this mixture over this composition range.

EXAMPLE 2

This example illustrates the use of the mixtures according to the invention as refrigerant fluids. The coefficients of performance of the mixtures according to the invention have been compared with the coefficients of performance of each constituent by itself, in the case of a standard thermodynamic cycle defined as follows:
- condensation temperature : +30° C.
- evaporation temperature : −20° C.
- liquid supercooling : +0° C.
- vapor superheating : +0° C.

Figure 2:
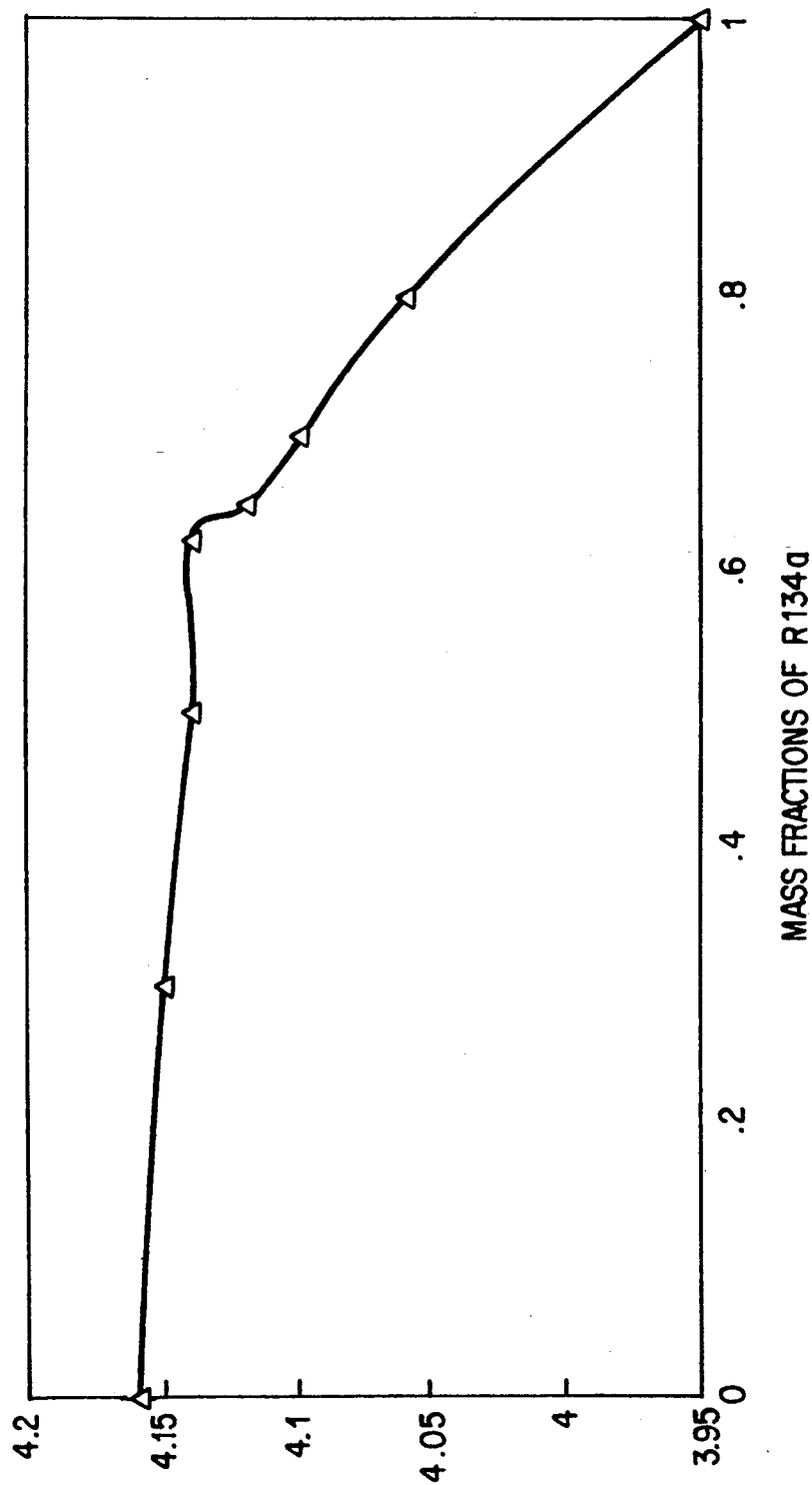
FIG. 2 is ia graph showing the Coefficient of Performance (COP) for DME mixtures.

FIG. 2 contains a graph which illustrates these results. The abscissa axis shows the mass fraction of HFA 134a and the ordinate axis the value of the COP.

It can be seen that in the case of mass fractions of HFA 134a which are lower than 65% the COP of the refrigerant mixture remains exceptionally stable, 4-5% higher than that of HFA 134a.

Table 3, which follows, compares, in the case of the same cycle, the coefficients of performance of the azeotrope according to the invention with those of pure HFA 134a and pure CFC 12.

TABLE 3

| | COP |
|---|---|
| CFC 12 | 4.03 |
| HFA 134a | 3.97 |
| DME/HFA 134a azeotrope | 4.14 |

It can be seen that the azeotropic mixture (apart from the advantage which it offers when compared with pure HFA 134a) also has a value of COP which is 3% higher (in the case of the cycle investigated here), when compared with the value of COP of pure CFC 12.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. An azeotropic mixture of dimethyl ether and 1,1,1,2-tetrafluoroethane which, at 1.013 bar, boils at about −22.4° C. and consists of about 62.3 mass % of 1,1,1,2-tetrafluorethane and 37.7 mass % of dimethyl ether.

2. A method of refrigeration comprising condensing and evaporating the mixture of claim 1.

3. A method of preparing an aerosol utilizing the propellant mixture of claim 1.

4. A method of manufacturing plastic foams utilizing the blowing agent mixture of claim 1.

* * * * *